United States Patent [19]

Palladino

[11] 4,031,080

[45] June 21, 1977

[54] 16-ALPHA-METHYL-17 ALPHA-BROMO-1,4-PREGNADIENE-21-OL-3,20-DIONE-DERIVATIVES

[75] Inventor: Gaetano Palladino, Milan, Italy

[73] Assignee: Lark S.p.A., Milan, Italy

[22] Filed: Jan. 29, 1976

[21] Appl. No.: 653,612

[30] Foreign Application Priority Data

Feb. 1, 1975  United Kingdom ............... 4473/75

[52] U.S. Cl. .................. 260/239.55 R; 260/397.45
[51] Int. Cl. .......................................... C07j 17/00
[58] Field of Search ..... /Machine Searched Steroids

[56] References Cited

UNITED STATES PATENTS 3,261,851  7/1966  Beal et al. ..................... 260/397.3
3,350,427  10/1967  Gebert et al. .................. 260/397.4

Primary Examiner—Elbert L. Roberts
Attorney, Agent, or Firm—Stevens, Davis, Miller & Mosher

[57] ABSTRACT

There is disclosed 16 alpha-methyl-17 alpha-bromo-1,4-pregnadiene-21-ol-3,20-dione-type compounds of the formula

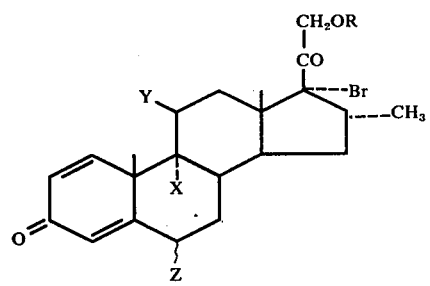

where R is hydrogen or acyl; X is hydrogen, bromine, or fluorine; Y is hydrogen or oxygen; and Z is hydrogen or α- or β-oriented fluorine. The compounds are useful in treating rheumatoid arthritis and related inflammatory disorders as well as allergic diseases.

11 Claims, No Drawings

16-ALPHA-METHYL-17 ALPHA-BROMO-1,4-PREGNADIENE-21-OL-3,20-DIONE-DERIVATIVES

This invention relates to new prednisolone-and prednisone-derivatives and to processes for their preparation.

More particularly, the invention relates to a new series of 16 alpha-methyl-17 alpha-bromo-1,4-pregnadiene-21-ol-3,20-dione-derivatives of the structure: g

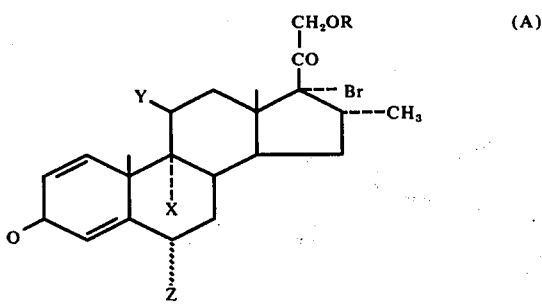

selected from the group consisting of hydrogen, hydroxyl bromine and fluorine atoms, Y is a member selected from the group consisting of hydrogen and oxygen, Z is a member selected from the group consisting of hydrogen and α- or β- oriented fluorine atoms.

The foregoing compounds possess chemoterapeutic utility in the treatment of rheumatoid arthritis and similar inflammatory disorders and of allergic diseases.

They are suitable for oral, parenteral and topic use and they are practically exempt from the well-known side-effects induced through use of corticosteroids available today. The compounds of the present invention of the structure (A), characterized by the functional grouping 16alpha-methyl-17alpha-bromo-1,4-pregnadiene-21-ol-3,20-dione, are to be considered quite original and they have not as yet been described in the literature.

To our best knowledge, the unique example of a 17alpha-bromo-derivative of a 16alpha-methyl-pregnane is the 17alpha-bromo-16alpha-methyl-progesterone (J. Org. Chem. 1967 page 2321).

A further object of the present invention is the process for their preparation. The new processes of the present invention may be illustratively represented by Scheme 1 and Scheme 2 as follows:

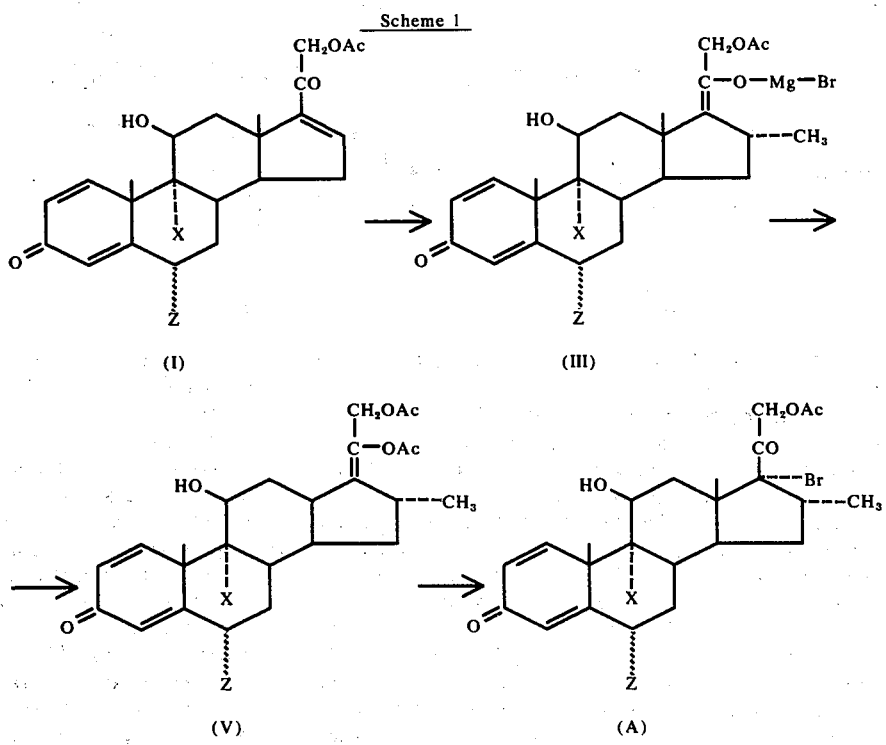

wherein R is a member selected from the group consisting of hydrogen and an acyl radical, X is a member wherein Ac is the acetyl group and X and Z have the above indicated meaning.

Scheme 2

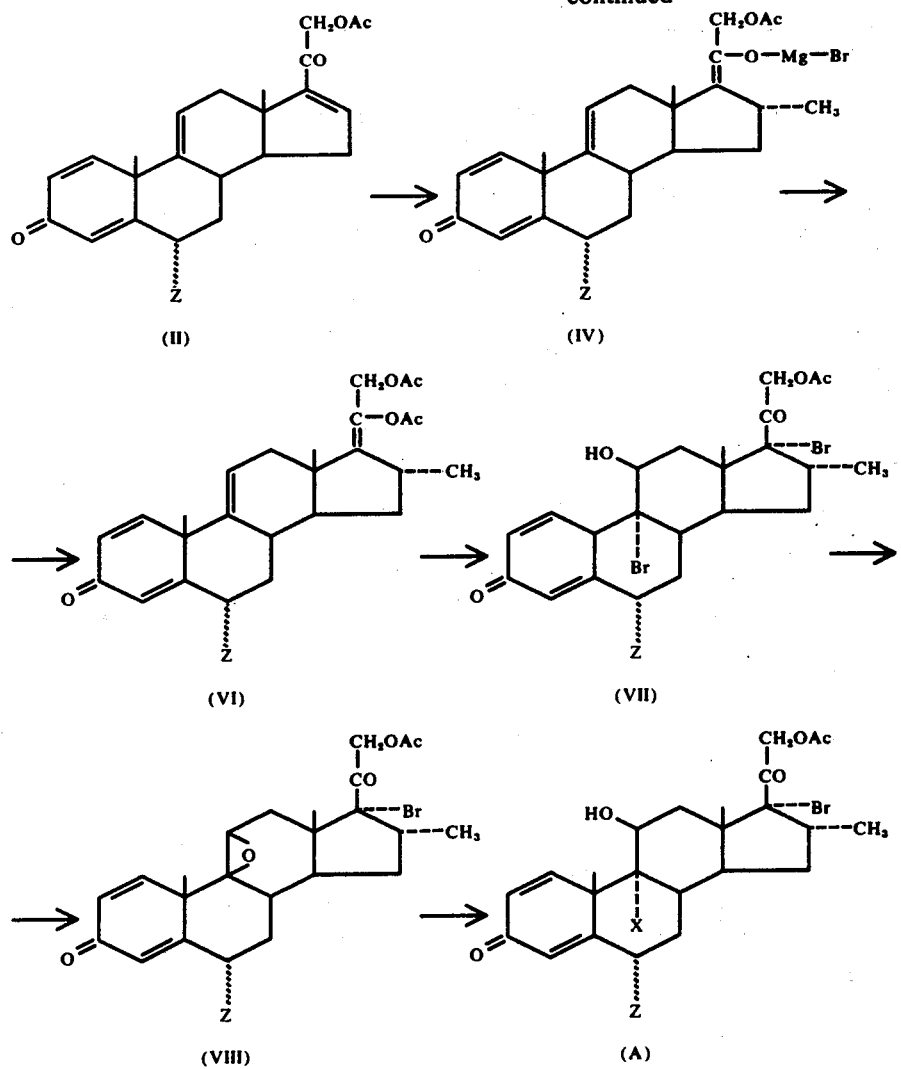

wherein Ac and Z have the above indicated meaning, and X is fluorine.

The starting compounds (I) and (II) may easily be prepared according to known procedures.

The starting compounds (I) and (II) are submitted to a standard Grignard reagent, for example methyl magnesium bromide or iodide, in tetrahydrofuran and in the presence of cuprous chloride to form the corresponding 16alpha-methyl-20-enol-derivative (III) and (IV). Upon reacting the latter compounds (III) and (IV) with a suitable acetylating agent, for instance acetyl chloride, the corresponding enol-acetates (V) and (VI) are obtained. These enolacetates (V) and (VI) are dissolved in tetrahydrofuran or in dioxane and are then reacted with an N-bromo-amide preferably N-bromo-acetamide or dibromo-dimethyl-hydantoin in the presence of perchloric acid to give the desired end product A (see Scheme 1) and respectively the intermediate (VII) (see Scheme 2). From this intermediate (VII) through the corresponding 9beta, 11beta-epoxide (VII) according to procedures known to those skilled in the art the desired end products (A) are obtained. The Grignard reaction performed on $\Delta^{16}$-pregnene-derivatives is well known from the literature. However, Grignard reactions performed on a $\Delta^{16}$-pregnene-derivative having also a 3-keto-$\Delta^{1,4}$- or a 3-keto-$\Delta^{1,4,9(11)}$-grouping have never been reported in the literature.

The best conditions so as to achieve the complete methylation as well as to prevent the hydrolysis of the 21-acetate-group are the use of from 20 to 30 ml of tetrahydrofuran for each gram of the starting compound and the use of from 2.5 to 3.0 moles of methylmagnesium bromide for each mole of the starting compound in the presence of 0.1 gram of cuprous chloride for each gram of the starting compound. As to the temperature range, the best results were achieved between −20° and 0° C.

Moreover, it is indispensable to purge the solution of oxygen by a continuous bubbling of nitrogen. The presence of oxygen was proved to bring about the formation of undesired by-products which prevent the subsequent reaction.

When the Grignard reaction is over (10 to 30 minutes) and at a temperature of −10° C, a cooled solution of acetyl-chloride in tetrahydrofuran is added to the reaction mass, in a molar ratio of 1.5 to 1.6 with respect to the starting compounds (I) and II).

The time necessary to complete the reaction of enol-acetylation is comprised between 10 and 60 minutes. When enol-acetylation is over the reaction mixture is slowly poured onto an aqueous solution of ammonium chloride contained in a suitable separatory funnel and the product is then extracted with ethyl ether.

From the ether extracts the intermediates (V) and (VI) may be recovered by evaporating off the solvent, by taking up the oily residue with methanol and by adding some water.

However, for the subsequent step (bromination it is not necessary to isolate said intermediates, but the above mentioned oily residue can be directly dissolved in dioxane or tetrahydrofuran and reacted with a suitable N-bromo-amide, preferably N-bromo-acetamide or dibromo-dimethyl-hydantoin in the presence of perchloric acid and at room temperature.

The 9beta, 11beta-epoxide-derivative (VIII) is prepared by reacting the corresponding bromhydrin-derivative (VII) dissolved in acetone or tetrahydrofuran with an aqueous solution of potassium carbonate or acetate at room temperature. The epoxide ring of compound (VIII) is opened by means of 70% aqueous hydrofluoric acid at temperatures between $-20°$ C and $0°$ C to give the desired end product (A).

The 11-keto-derivatives comprised by the general formula of end product (A), in which Y = oxygen, may be prepared by oxydizing the corresponding 11beta-hydroxy-derivatives with alkali chromates in acetic acid or with $CrO_3$.

The 21-acetyl-ester-group of end products or of some intermediates may be hydrolized according to procedures known per se to the 21- free alcohol group, and this latter may - in its turn - be converted into a suitable 21-acyl-ester-group derived from an inorganic or organic mono- and dicarboxylic acid. The following Examples are illustrative of the procedures and products of the present invention, but they are not to be construed as limiting the scope thereof.

EXAMPLE 1

9alpha; 17alpha-dibromo-16alpha-methyl-1,4-pregnadiene-11beta, 21-diol-3,20-dione-21-acetate (VII, Z = H)

A suspension of 0.5 g of cuprous chloride in a solution of 5 g of 1,4,9 (11),16-pregnatetraene-21-ol-3,20-dione-21-acetate (II, Z = H) in 100 ml of anhydrous peroxide-free tetrahydrofuran was purged of oxygen by bubbling nitrogen therethrough for about three minutes. To this suspension cooled to $-15°$ C a Grignard reagent prepared with methyl bromide and 1,2 g magnesium in 60 ml anhydrous tetrahydrofuran was added over a 30 minutes period with stirring. After a further 5 minute stirring 1.7 g of acetyl chloride dissolved in 17 ml of anhydrous tetrahydrofuran were added dropwise.

Stirring at $0°$ to $5°$ C was continued for a further 30 minutes, then the mixture was poured onto 80 ml of a 10% aqueous ammonium chloride. The product thus separated was extracted with ethyl ether. The ether extracts were combined, dried over anhydrous sodium sulfate and concentrated in vacuo to dryness. The semisolid residue consisting of the crude 16alpha-methyl-20-enol-acetate (VI, Z = H) was dissolved in 50 ml of tetrahydrofuran and reacted with 7 ml of 7% of perchloric acid and 2.5 g of dibromo-dimethyl-hydantoin at 20 to $25°$ C. and the reaction mixture was kept under stirring for a further hour. Then the excess of the brominating agent was destroyed by adding a 10% aqueous solution of sodium sulfite, and the reaction mixture was poured on 500 ml of cold water. The product was filtered, washed with water and vacuum-dried at $35°$ C.

Yield 7 g of crude compound (VII, Z = H).

Upon crystallization from methanol 5.5 g of 9alpha, 17alpha-dibromo-16alpha-methyl-1,4-pregnadiene-11beta, 21-diol-3,20-dione-21-acetate (VII, Z = H) were obtained.

UV/spectrum $\lambda_{max}^{MeOH}$ 242m$\mu$; $E_{1\ cm}^{1=} = 250$ $[\alpha]_D = +32.2°$ (c=1 in dioxane)

IR-spectrum (KBr) 1748, 1730, 1659, 1618 (s) 1606, 1297, 1244, 1042 cm$^{-1}$.

Empirical formula: $C_{24}H_{30}Br_2O_5$ Calculated Bromine 28.62% ; Found Bromine 28.90%

EXAMPLE 2

9beta, 11beta-epoxy-16alpha-methyl-17alpha-bromo-1,4-pregnadiene-21-ol-3,20-dione-21-acetate (VIII, Z = H)

To a solution of 11,5 g of the bromhydrine (VII, Z = H) obtained according to Example 1., in 460 ml of tetrahydrofuran there were slowly added 4.6 g of potassium carbonate dissolved in 290 ml of water with stirring. The reaction mixture was kept for 2 hours at about $20°$ to $25°$ C under stirring. Addition of 29 g of sodium chloride caused the reaction mixture to separate into two layers: the upper one, containing the desired product, was then dried over anhydrous sodium solfate and evaporated in vacuo to dryness. The residue gave on crystallization from methanol-water 7.2 g of 9beta, 11beta-epoxy-16alpha-methyl-17alpha-bromo-1,4-pregnadiene-21-ol-3,20-dione-21-acetate.

UV/spectrum $\lambda_{max}^{MeOH}$ 248.5m$\mu$; $E_{1\ cm}^{1=} = 328$ $[\alpha]_D = -81.2°$ (c =1 dioxane)

IR-Spectrum (KBr) 1750, 1722, 1664, 1618, 1607, 1237 cm$^{-1}$

Empirical formula: $C_{24}H_{29}BrO_5$; Calculated Bromine: 16.74%; Found Bromine: 16.80%.

EXAMPLE 3

9beta, 11beta-epoxy-16alpha-methyl-17alpha-bromo-1,4-pregnadiene-21-ol-3,20-dione-21-acetate (VII, Z = H) To a solution of 1 g of the bromhydrine (VII, Z = H) obtained according to Example 1., in 10 ml of acetone 3 g of potassium acetate were added and the solution was refluxed for 90 minutes. It was then cooled to $20°$ C and poured in 100 ml of water. The product thus precipitated was filtered and washed with water. The crude wet product was crystallized from methanol-water. 0.6 g of pure 9beta, 11beta-epoxy-16alpha-methyl-17alpha-bromo-1,4-pregnadiene-21-ol-3,20-dione-21-acetate were obtained having the same characteristics of the same prepared according to Example 2.

EXAMPLE 4

9alpha-fluoro-16alpha-methyl-17alpha-bromo-1,4-pregnadiene-11beta,21-diol-3,20-dione-21-acetate (A in which R=Ac; X=F; Y=OH; Z=H)

In a polyethylene vessel containing 35 ml of 70% hydrofluoric acid cooled to $-15°$ C 7 g of 9beta, 11beta-epoxy-16alpha-methyl-17alpha-bromo-1,4-pregnadiene-21-ol-3,20-dione-21-acetate were added over a 15 minutes period with stirring. The reaction mixture was kept under stirring for one hour, then it was slowly poured in a separatory funnel containing 560 ml of icy water, 63 ml of 30% aqueous ammonia and 200 ml of ethyl acetate. The mixture was thoroughly shaken and allowed to separate.

The upper layer was then dried over anhydrous sodium sulfate and concentrated in vacuo to dryness. The residue was dissolved in chloroform and passed through a chromatographic column on silica-gel. The column was then eluted with chloroform containing 2% of acetone. The solution thus obtained was evaporated to a small volume to give 4 g of 9alpha-fluoro-16alpha-methyl-17alpha-bromo-1,4-pregnadiene-11beta,21-diol-3,20-dione-21-acetate.

UV-Spectrum $\lambda_{max}^{MeOH}$ 239.4 m$\mu$; $E_1\ _{cm}^{1\%}$ = 314

[$\alpha$]$_D$ = − 10.3° (c = 1 dioxane)

IR-Spectrum (KBr) 1750, 1720, 1663, 1618; 1605,1297, 1232, 1110 cm$^{-1}$

Empirical formula: $C_{24}H_{30}BrFO_5$; Calculated: Fluorine 3.82%; Bromine 16.06%; Found: Fluorin 3.78%; Bromine 16.1%;

EXAMPLE 5

9alpha, 17alpha-dibromo-16alpha-methyl-1,4-pregnadiene-11beta, 21-diol-3,20-dione ( VII - 21 - hydroxy; Z =H)

To a suspension of 5 g of bromhydrine (VII; Z =H) in 50 ml of methanol 1 ml of 70% perchloric acid was added. The suspension was kept for 24 hours under stirring at room temperature. After 12 hours it was observed a complete solubilization, whereupon the bromhydrine-21-alcohol precipitated.

The precipitate was filtered, washed with little methanol and dried at 35° C in vacuo. Yield 2.7 g of 9alpha, 17alpha-dibromo-16alpha-methyl-1,4-pregnadiene-11beta, 21-diol-3,20-dione.

UV-Spectrum $\lambda_{max}^{MeOH}$ = 242 m$\mu$; $E_1\ _{cm}^{1\%}$ = 275

[$\alpha$]$_D$ = + 39,3° (c = 1 dioxane)

IR-Spectrum (KBr) 1706, 1658, 1618 (s), 1608, 1298, 1104, 1070, 1040 cm$^{-1}$

Empirical formula: $C_{22}H_{28}BrO_4$. Calculated: Bromine 30.96 %; Found: Bromine 31.2 %.

EXAMPLE 6

9beta, 11beta-epoxy-16alpha-methyl-17alpha-bromo-1,4-pregnadiene-21-ol-3,20-dione ( VIII - 21 - hydroxy; Z = H)

By starting from the bromhydrine (VII-21-hydroxy; Z =H) obtained according to Example 5. and by following either the method illustrated in Example 2. or the method illustrated in Example 3., the compound 9beta, 11beta-epoxy-16alpha-methyl-17alpha-bromo-1,4-pregnadiene-21-ol-3,20-dione was obtained having the following characteristics:

UV-Spectrum $\lambda_{max}^{MeOH}$ = 248,49 m$\mu$; $E_{1m}^{1\%}$ = 359

[$\alpha$]$_D$ = − 79,7° (c = 1 dioxane)

IR-Spectrum (KBr) 1712, 1662; 1621, 1607, 1060 (s), 1100 cm$^{-1}$

Empirical formula : $C_{22}H_{27}BrO_4$. Calculated; Bromine 18,35 %; Found: Bromine 18,50 %.

EXAMPLE 7

9alpha-fluoro-16alpha-methyl-17alpha-bromo-1,4-pregnadiene-11beta, 21-diol-3,20-dione (A - 21 - hydroxy; X =F; Y =OH; Z =H )

By starting from the 9beta, 11beta-epoxy-derivative (VIII-21-hydroxy; Z = H) obtained according to Example 6. and by following the method illustrated in Example 4. the compound 9alpha-fluoro-16alpha-methyl-17alpha-bromo-1,4-pregnadiene-11beta,21-diol-3,20-dione was obtained having the following characteristics UV-Spectrum $\lambda_{max}^{MeOH}$ =239,4 m$\mu$; $E_1\ _{cm}^{1\%}$ = 343

[$\alpha$]$_D$ = −51° (c = 1 dioxane)

IR-Spectrum (KBr) 1708, 1662, 1619, 1607, 1096 (s), 1090 (s), 1046 (s)

Empirical formula : $C_{22}H_{28}BrFO_4$. Calculated; Fluorine 4,17 %, Bromine 17,55%; Found; Fluorine 4,08%, Bromine 17,45 %.

EXAMPLE 8

6beta-fluoro-9alpha,17alpha-dibromo-16alpha-methyl-1,4-pregnadiene-11beta,21-diol-3,20-dione-21-acetate. (VII, Z = Beta F)

By starting from 6beta-fluoro-1,4,9(11),16 (17)-pregnatetraene-21-ol-3,20-dione-21-acetate (Compound II, Z = Beta F) and by following the method illustrated in EXAMPLE 1. the compound 6beta-fluoro-9alpha,17alpha-dibromo-16alpha-methyl-1,4-pregnadiene-11beta,21-diol-3,20-dione-21-acetate was obtained showing the following characteristics :

UV-Spectrum $\lambda_{max}^{MeOH}$ = 241-242 m$\mu$; $E_1\ _{cm}^{1\%}$ = 246

[$\alpha$]$_D$ = −22,4° (c = 1 dioxan)

IR-Spectrum (KB) 1746 - 1721 - 1665 - 1628 - 1296 - 1232 - 1042 cm$^{-1}$

Empiral formula : $C_{24}H_{29}Br_2FO_5$, Calculated: Bromine 27,7%; Found: Bromine 28,4%,

EXAMPLE 9

6beta-fluoro-9beta,11beta-epoxy-16alpha-methyl-17alpha-bromo-1,4-pregnadiene-21-ol-3,20-dione. (VIII 21-ol; Z = Beta F )

By using the bromhydrine VII ( Z = Beta F) and by following the procedure illustrated in EXAMPLE 3, but wherein acetone was replaced by 90% aqueous methanol, 6beta-fluoro-9beta, 11beta-epoxy-16alpha-methyl-17alpha-bromo-1,4-pregnadiene-21-ol-3,20-dione was obtained having the following characteristics:

UV-Spectrum $\lambda_{max}^{MeOH}$ 248 − 249 m$\mu$; $E_1\ _{cm}^{1\%}$ = 315

IR-Spectrum (K Br) 1712 - 1667 - 1633 - 1050 cm$^{-1}$

EXAMPLE 10

6beta, 9alpha-difluoro-16alpha-methyl-17alpha-bromo-1,4-pregnadiene-11beta, 21-diol-3,20-dione (A 21-OH; X =F; Y =OH; Z =Beta F)

By starting from the compound obtained according to EXAMPLE 9 and by following the procedure illustrated in EXAMPLE 4, 6beta, 9alpha-difluoro-11alpha-methyl-17alpha-bromo-1,4-pregnadiene-11beta,21-diol-3,20-dione was obtained, having the following characteristics :

UV-Spectrum $\lambda_{max}^{MeOH}$ 239 - 240 m$\mu$; $E_1\ _{cm}^{1\%}$ = 342

[$\alpha$]$_D$ = −55° (c = 1 dioxan )

IR-Spectrum (K Br) 1710 - 1668 - 1631 - 1298 - 1033 cm$^{-1}$ Empirical formula : $C_{22}H_{27}BrF_3O_4$, Calculated Bromine : 16.9 %; Found Bromine : 17,25 %,

EXAMPLE 11

6beta, 9alpha-difluoro-16alpha-methyl-17alpha-bromo-1,4pregnadiene-11beta, 21-diol-3,20-dione-21-acetate ( A; X =F; Y =OH; Z =Beta F)

By acylating the product prepared according to EXAMPLE 10, 6beta, 9alpha-difluoro-16alpha-methyl-17alpha-bromo-1,4-pregnadiene-11beta,21-diol-3,20-dione-21-acetate was obtained showing the following characteristics:

UV-Spectrum $\lambda_{max}^{MeOH}$ 239–240 m$\mu$; $E_1{}_{cm}^{1\%}$ = 305

$[\alpha]_D = -50,8°$ ( c = 1 dioxan )

IR-Spectrum ( K Br ) 1754 - 1722 - 1668 - 1628 - 1234 - 1036 cm$^{-1}$

What we claim is:

1. A 16alpha-methyl-17alpha-bromo-1,4-pregnadiene-21-ol-3,20 -dione-derivative of the structure :

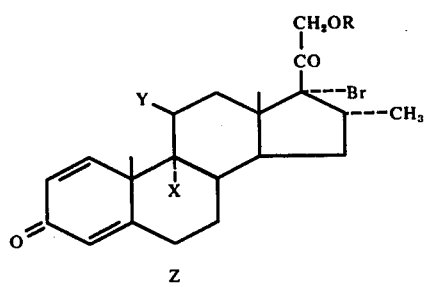

wherein R is a member selected from the group consisting of hydrogen and an acyl radical, X is a member selected from the group consisting of hydrogen, bromine and fluorine atoms, Y is a member selected from the group consisting of hydrogen hydroxyl and oxygen, Z is a member selected from the group consisting of hydrogen, and alpha- or beta-oriented fluorine atoms.

2. 9alpha, 17alpha-dibromo-16alpha-methyl-1,4-pregnadiene-11beta,21-diol-3,20-dione-21-acetate.

3. 9beta,11beta-epoxy-16alpha-methyl-17alpha-bromo-1,4-pregnadiene-21-ol-3,20-dione-21-acetate.

4. 9alpha-fluoro-16alpha-methyl-17alpha-bromo-1,4-pregnadiene-11beta,21-diol-3,20-dione.

5. 9alpha,17alpha-dibromo-16alpha-methyl-1,4-pregnadiene-11beta, 21diol-3,20dione.

6. 9beta,11beta-epoxy-16alpha-methyl-17alpha-bromo-1,4-pregnadiene-21-ol-3,20-dione.

7. 9alpha-fluoro-16alpha-methyl-17alpha-bromo-1,4-pregnadiene-11beta,21-diol-3,20-dione.

8. 6beta-fluoro-9alpha, 17alpha-dibromo-16alpha-methyl-1, 4-pregnadiene-11beta,21-diol-3,20-dione-21-acetate.

9. 6beta-fluoro-9beta,11beta-epoxy-16alpha-methyl-17alpha-bromo-1,4-pregnadiene-21-ol-3,20-dione.

10. 6beta, 9alpha-difluoro-16alpha-methyl-17alpha-bromo-1,4-pregnadiene-11beta, 21-diol-3,20-dione.

11. 6beta,9alpha-difluoro-16alpha-methyl-17alpha-bromo-1,4-pregnadiene-11beta,21-diol-3,20-dione-21-acetate.

* * * * *

UNITED STATES PATENT AND TRADEMARK OFFICE
CERTIFICATE OF CORRECTION

PATENT NO. : 4,031,080
DATED : June 21, 1977
INVENTOR(S) : Gaetano PALLADINO

It is certified that error appears in the above-identified patent and that said Letters Patent are hereby corrected as shown below:

In the Abstract, second line after the structural formula, delete "hydrogen" and insert in its place --hydroxyl--;

Column 2, delete the word "hydroxyl" bridging lines 1 and 2;

Column 2, line 3, after "hydrogen" insert --, hydroxyl--;

Column 3, line 63, delete "(VII)" and insert in its place --(VIII)--;

Column 6, line 6, delete "$E_1 \, _{cm}^{1=} = 250$" and insert in its place --$E \, _{1cm}^{1\%} = 250$--;

Column 6, line 31, delete "$E_1 \, _{cm}^{1=} = 328$" and insert in its place --$E \, _{1cm}^{1\%} = 328$--;

Column 6, line 41, delete "VII" and insert in its place --VIII--;

UNITED STATES PATENT AND TRADEMARK OFFICE
CERTIFICATE OF CORRECTION

PATENT NO. : 4,031,080
DATED : June 21, 1977
INVENTOR(S) : Gaetano PALLADINO

It is certified that error appears in the above-identified patent and that said Letters Patent are hereby corrected as shown below:

Column 9, claim 1, in the last line of the structural formula, attach Z to the compound ring above it as follows:

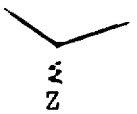

Signed and Sealed this

Thirteenth Day of December 1977

[SEAL]

Attest:

RUTH C. MASON
*Attesting Officer*

LUTRELLE F. PARKER
*Acting Commissioner of Patents and Trademarks*